(12) United States Patent
Foelling

(10) Patent No.: US 9,179,131 B2
(45) Date of Patent: Nov. 3, 2015

(54) MICROSCOPIC DEVICE AND METHOD FOR THREE-DIMENSIONAL LOCALIZATION OF POINT-LIKE OBJECTS IN A SPECIMEN

(71) Applicant: Leica Microsystems CMS GmbH, Wetzlar (DE)

(72) Inventor: Jonas Foelling, Heidelberg (DE)

(73) Assignee: LEICA MICROSYSTEMS CMS GMBH, Wetzlar (DE)

( * ) Notice: Subject to any disclaimer, the term of this patent is extended or adjusted under 35 U.S.C. 154(b) by 447 days.

(21) Appl. No.: 13/672,881

(22) Filed: Nov. 9, 2012

(65) Prior Publication Data
US 2013/0120539 A1 May 16, 2013

(30) Foreign Application Priority Data
Nov. 11, 2011 (DE) .......................... 10 2011 055 294

(51) Int. Cl.
| | |
|---|---|
| *H04N 15/00* | (2006.01) |
| *A61B 1/06* | (2006.01) |
| *H04N 13/02* | (2006.01) |
| *G02B 27/00* | (2006.01) |

(Continued)

(52) U.S. Cl.
CPC ....... *H04N 13/0257* (2013.01); *G01N 21/6458* (2013.01); *G02B 21/16* (2013.01); *G02B 21/367* (2013.01); *G02B 27/0075* (2013.01); *G02B 27/58* (2013.01); *G01N 2021/6421* (2013.01)

(58) Field of Classification Search
USPC ................................................ 348/42–60, 79
See application file for complete search history.

(56) References Cited

U.S. PATENT DOCUMENTS

| | | | |
|---|---|---|---|
| 5,896,224 | A | 4/1999 | Kapitza |
| 6,628,385 | B1 | 9/2003 | Osipchuk et al. |

(Continued)

FOREIGN PATENT DOCUMENTS

| | | |
|---|---|---|
| DE | 10004191 A1 | 12/2000 |
| DE | 10319659 A1 | 11/2004 |

(Continued)

OTHER PUBLICATIONS

M. J. Rust, M. Bates, X. Zhuang, "Sub-diffraction-limit imaging by stochastic optical reconstruction microscopy (STORM)," Nature Methods 3, p. 793-796, Oct. 2006.

(Continued)

*Primary Examiner* — Nigar Chowdhury
(74) *Attorney, Agent, or Firm* — Leydig, Voit & Mayer, Ltd.

(57) ABSTRACT

A microscopic device for three-dimensional localization of point-like objects, encompassing a detection optical system that images point-like objects, each in the form of a three-dimensional focus light distribution, into an image space; a color separation apparatus that divides the light into at least two separate light bundles of different wavelength regions; at least two image space detector units, one receiving one light bundle and the other receiving the other light bundle, each detector unit comprising a light-spot-sensing detection surface; an evaluation unit that ascertains a lateral X-Y position and an axial Z position relative to the sharpness plane in a direction perpendicular to the sharpness plane; at least one Z-position correction value for at least one of the wavelength regions being stored in the evaluation unit, which value indicates a detection optical system longitudinal chromatic aberration in that wavelength region; and the evaluation unit correcting the Z position.

19 Claims, 6 Drawing Sheets

(51) Int. Cl.
*G01N 21/64* (2006.01)
*G02B 21/16* (2006.01)
*G02B 21/36* (2006.01)
*G02B 27/58* (2006.01)

(56) References Cited

U.S. PATENT DOCUMENTS

| | | | |
|---|---|---|---|
| 6,631,226 | B1 | 10/2003 | Schoeppe et al. |
| 7,286,225 | B2 | 10/2007 | Aikawa |
| 2004/0238731 | A1 | 12/2004 | Nishiyama et al. |
| 2006/0011812 | A1 | 1/2006 | Wolleschensky et al. |
| 2008/0182336 | A1 | 7/2008 | Zhuang et al. |
| 2008/0317334 | A1* | 12/2008 | Hausler ............... 382/154 |
| 2009/0134342 | A1 | 5/2009 | Hell et al. |
| 2009/0296207 | A1 | 12/2009 | Goelles et al. |
| 2013/0010098 | A1 | 1/2013 | Kalkbrenner et al. |

FOREIGN PATENT DOCUMENTS

| | | |
|---|---|---|
| DE | 102004034974 A1 | 2/2006 |
| DE | 102004034980 A1 | 2/2006 |
| DE | 102005056663 A1 | 6/2006 |
| DE | 102005040827 A1 | 6/2007 |
| DE | 102006021317 B3 | 10/2007 |
| DE | 102008024568 A1 | 12/2009 |
| EP | 1015869 B1 | 4/2004 |
| EP | 2148188 A1 | 1/2010 |
| WO | 2006127692 A2 | 11/2006 |
| WO | 2007128434 A1 | 11/2007 |
| WO | 2008091296 A2 | 7/2008 |
| WO | 2009085218 A1 | 7/2009 |
| WO | 2010062364 A1 | 6/2010 |
| WO | 2011085766 A1 | 7/2011 |

OTHER PUBLICATIONS

Geisler C. et al, "Resolution of Lambda/10 in fluorescence microscopy using fast single molecule photo-switching," Appl. Phys. A, 88, p. 223-226, May 2007.
Kao et.al., Tracking of SotrogjH® Fluorescent Particles in Three Dimensions: Use of Cylindrical Optics to Encode Particle Position Sep. 1994, Biophysical Journal 67, p. 1291-1300.
Toprak et.al., Three-Dimensional Particle Tracking via Bifocal Imaging 2007, Nano Letters, Jun. 6, 2007 vol. 7, No. 7, p. 2043-2045.
Huang et.al., Three-Dimensional Super-Resolution Imaging by Stochastic Optical Reconstruction Microscopy, Feb. 8, 2008, Science, p. 810-813.
Holtzer et.al., 2007, Applied Physics Letters 90, Nanometric three-dimensional tracking of individual quantum dots in cells, Feb. 1, 2007.
Juette et.al., Three-dimensional sub-100 nm resolution fluorescence microscopy of thick samples, May 11, 2008, Nature Methods, p. 1-3.
Bossi et al., Multicolor Far-Field Fluorescence Nanoscopy through Isolated Detection of Distinct Molecular Species, Jul. 2008, Nano Letters, 8(8), p. 2463-2468.
Pavani et.al., Three-dimensional, single-molecule fluorescence imaging beyond the diffraction limit by using a double-helix point spread function, Mar. 3, 2009 PNAS, 106 (9), p. 2995-2999.

* cited by examiner

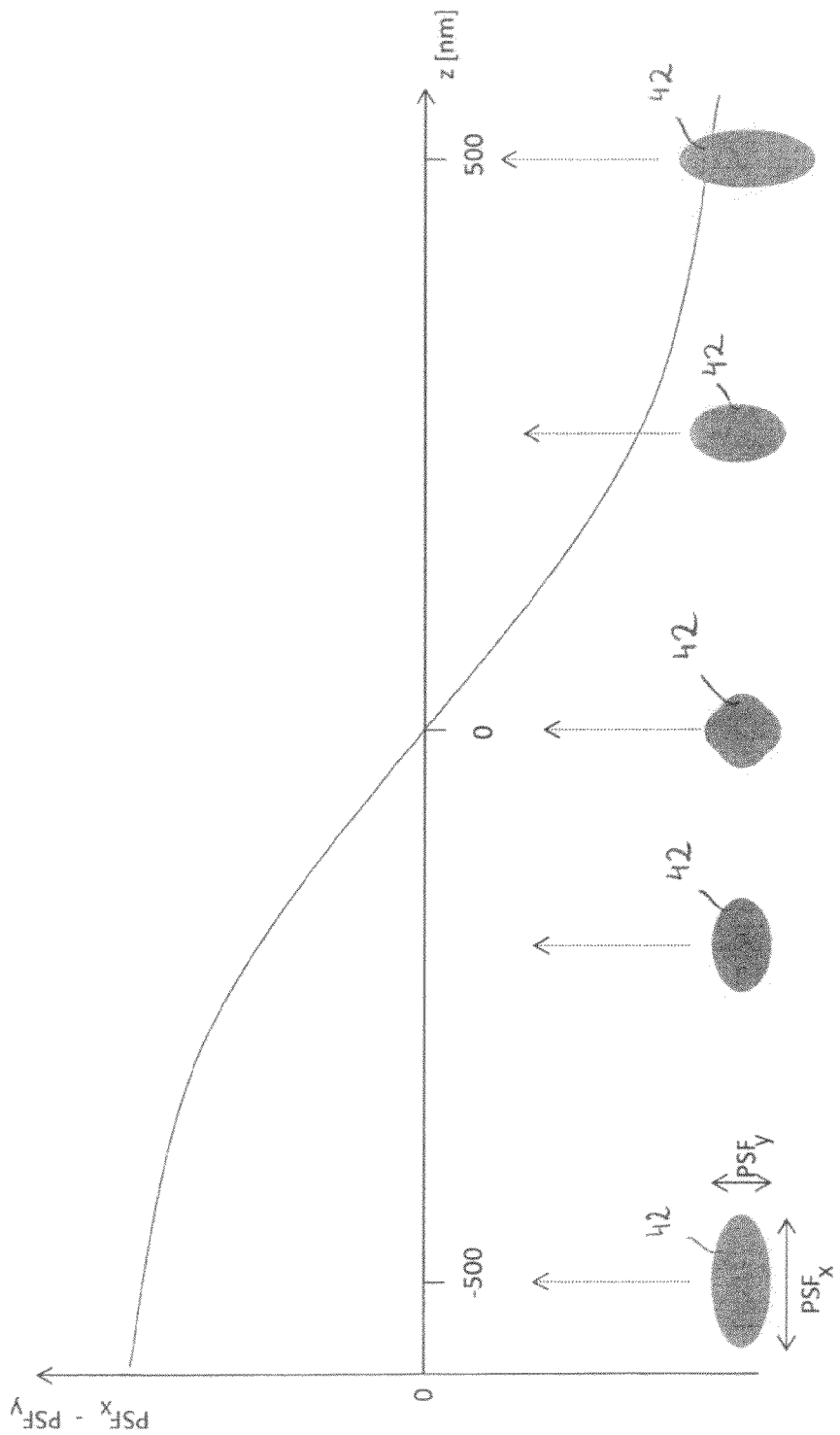

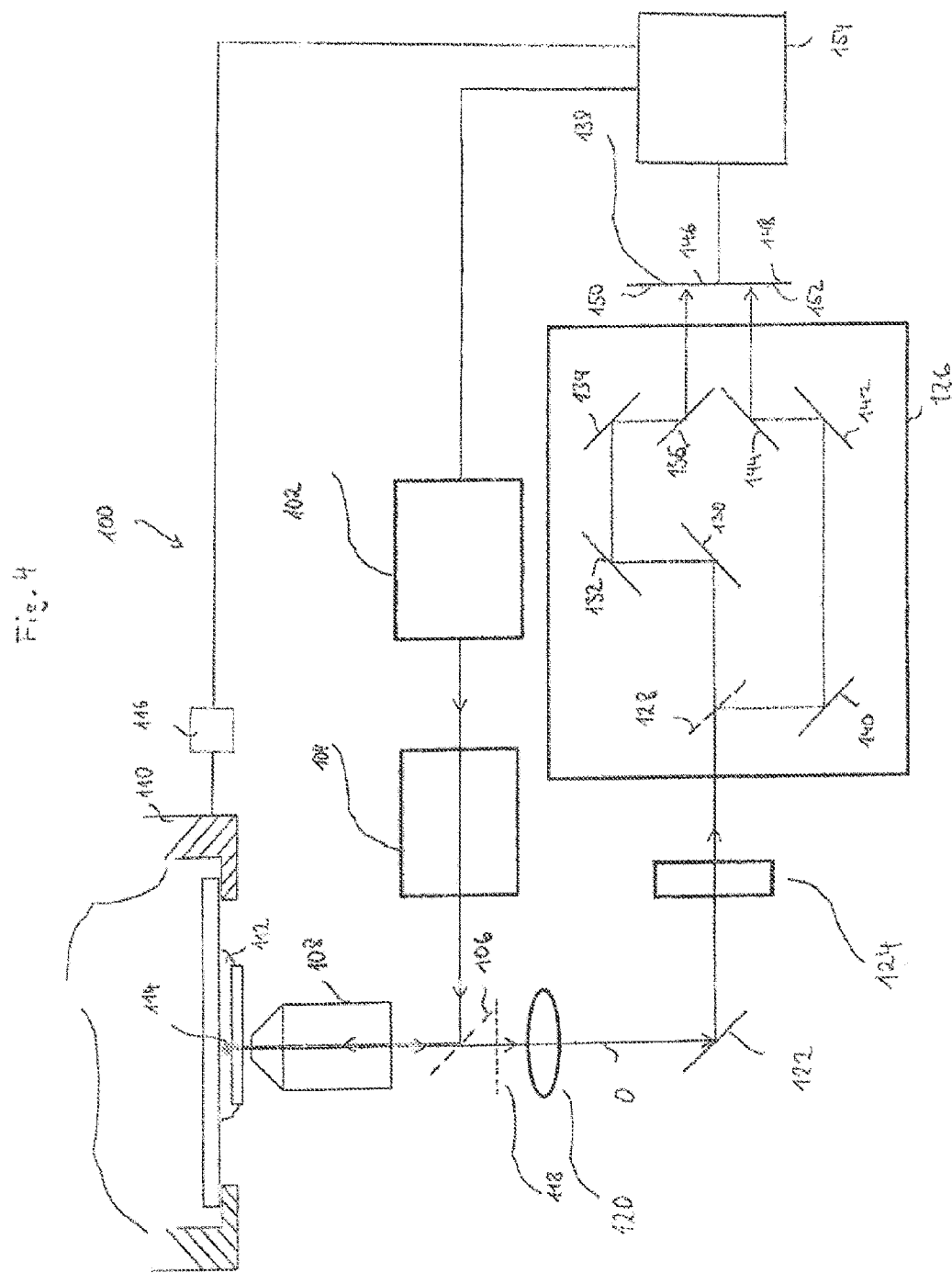

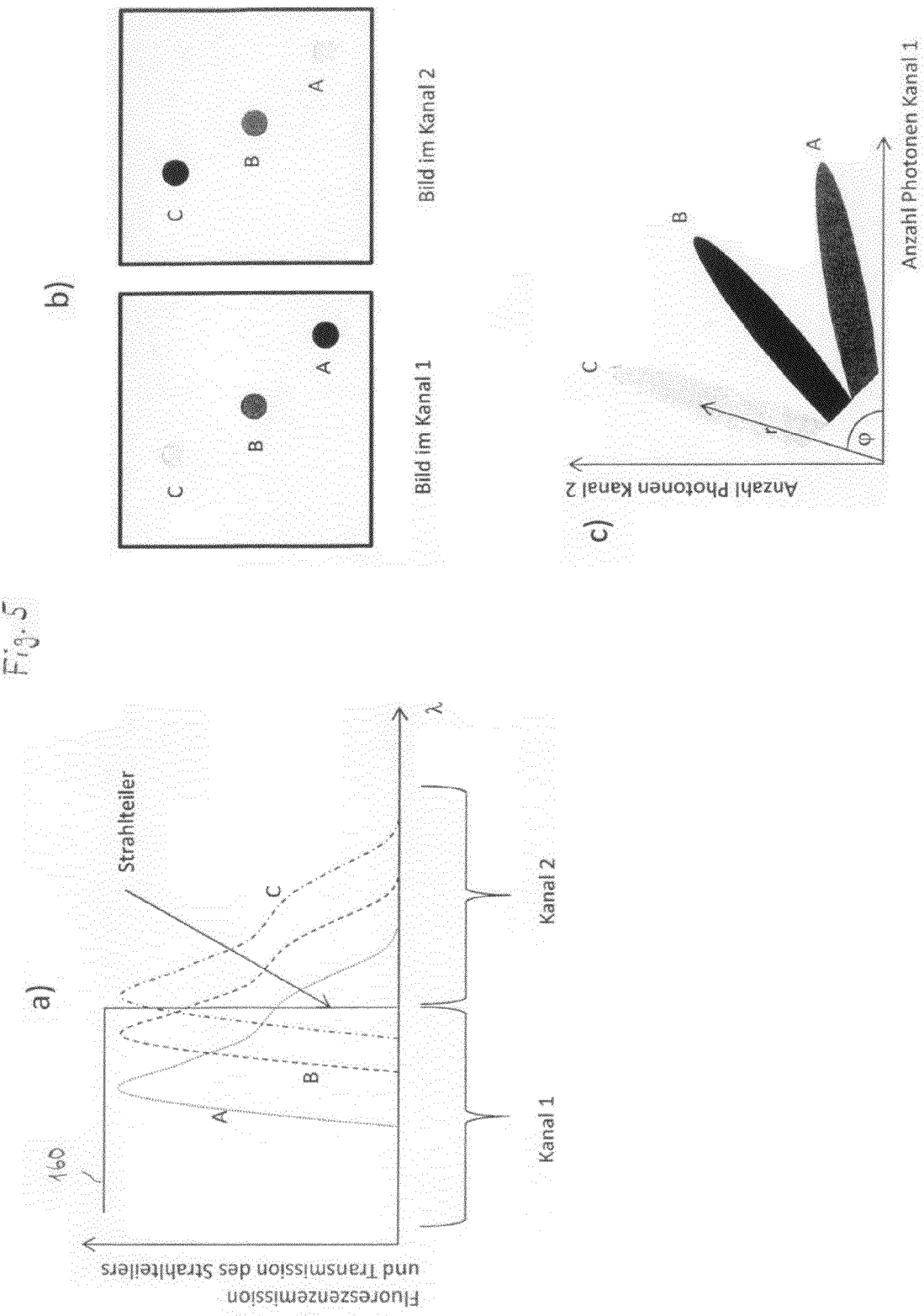

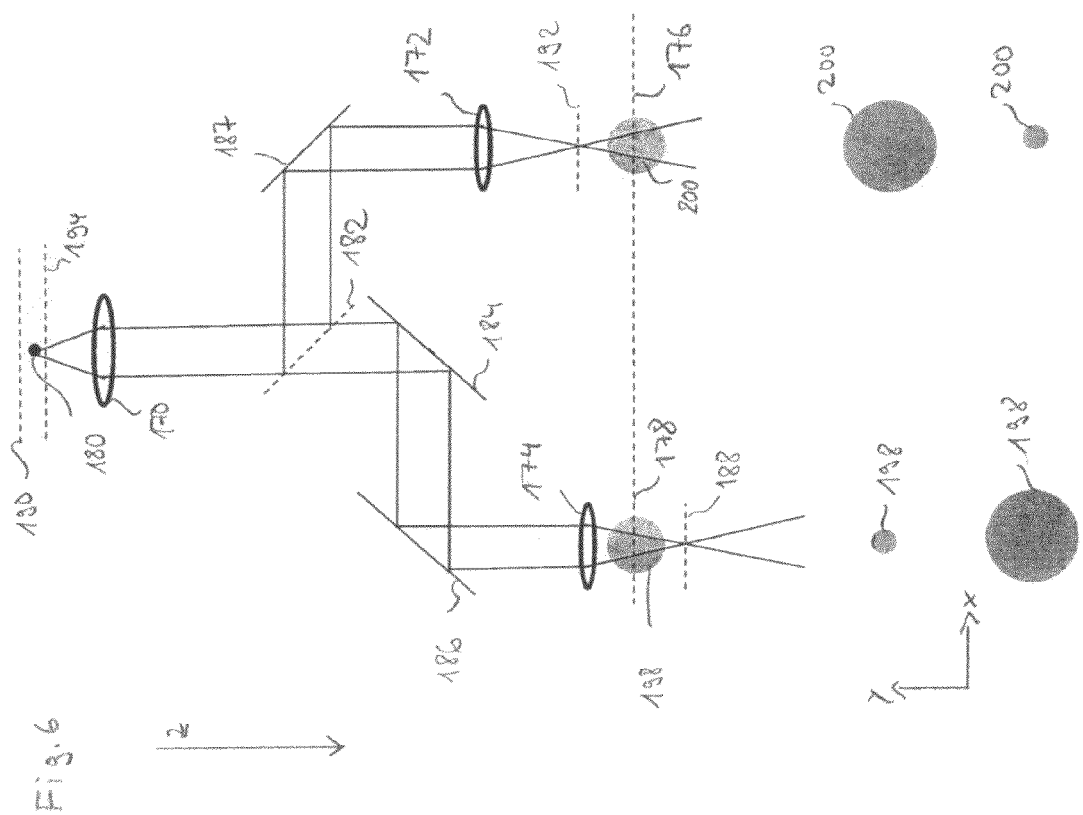

MICROSCOPIC DEVICE AND METHOD FOR THREE-DIMENSIONAL LOCALIZATION OF POINT-LIKE OBJECTS IN A SPECIMEN

CROSS REFERENCE TO RELATED APPLICATIONS

Priority is claimed to German Patent Application No. DE 10 2011 055 294.4, filed on Nov. 11, 2011, the entire disclosure of which is incorporated by reference herein.

FIELD

This application relates to light-microscopy methods which, based on a sequential, stochastic localization of individual markers, in particular fluorescent molecules, can display specimen structures that are smaller than the diffraction-limited resolution limit of classic light microscopes.

BACKGROUND

In the recent past, light-microscopy methods have been developed with which, based on a sequential, stochastic localization of individual markers, in particular fluorescent molecules, it is possible to display specimen structures that are smaller than the diffraction-limited resolution limit of classic light microscopes. Such methods are described, for example, in WO 2006/127692 A2; DE 10 2006 021 317 B3; WO 2007/128434 A1, US 2009/0134342 A1; DE 10 2008 024 568 A1; WO 2008/091296 A2; "Sub-diffraction-limit imaging by stochastic optical reconstruction microscopy (STORM)," Nature Methods 3, 793-796 (2006), M. J. Rust, M. Bates, X. Zhuang; "Resolution of Lambda/10 in fluorescence microscopy using fast single molecule photo-switching," Geisler C. et al, Appl. Phys. A, 88, 223-226 (2007). This new branch of microscopy is also referred to as "localization microscopy." The methods applied are known in the literature, for example, under the designations (F)PALM ((fluorescence) photoactivation localization microscopy), PALMIRA (PALM with independently running acquisition), GSD(IM) (ground state depletion (individual molecule return) microscopy), or (F)STORM ((fluorescence) stochastic optical reconstruction microscopy).

The new methods have in common the fact that the specimen structures to be imaged are prepared with point-like objects, called markers, that possess two distinguishable states, namely a "bright" state and a "dark" state. For example, if fluorescent dyes are used as markers, the bright state is then a fluorescence-capable state and the dark state is a non-fluorescence-capable state.

In preferred embodiments, for example in WO 2008/091296 A2 and WO 2006/127692 A2, photo-switchable or photoactivatable fluorescent molecules are used. Alternatively, as e.g. in DE 10 2006 021 317 B3, inherent dark states of standard fluorescent molecules can be used.

In order for specimen structures to be imaged at a resolution that is higher than the classic resolution limit of the image-producing optical system, a small subset of the markers is then repeatedly transferred into the bright state. The density of the markers constituting this active subset must be selected so that the average spacing between adjacent markers in the bright state and thus the state that can be imaged by light microscopy is greater than the resolution limit of the imaging optical system. The markers constituting the active subset are imaged onto a spatially resolving light detector, e.g. a CCD camera, so that a light distribution of each point-like marker is sensed in the form of a light spot whose size is determined by the resolution limit of the optical system.

A plurality of individual raw-data images are sensed in this manner, in each of which a different active subset is imaged. In an image analysis process, the center-point positions of the light distributions, representing the point-like markers that are in the bright state, are then determined in each individual raw-data image. The center-point positions of the light distributions ascertained from the individual raw-data images are then combined into one overall depiction in the form of an overall image data set. The high-resolution overall image produced by this overall depiction reflects the distribution of the markers.

For a representative reproduction of the specimen structure to be imaged, a sufficiently large number of marker signals must be detected. But because the number of markers in each active subset is limited by the minimum average spacing that must exist between two markers in the bright state, a very large number of individual raw-data images must be sensed in order to image the specimen structure completely. The number of individual raw-data images is typically in a range from 10,000 to 100,000.

In addition to the above-described determination of the lateral position of the markers in the object plane (hereinafter also referred to as the X-Y plane), a position determination in an axial direction (hereinafter also referred to as the Z direction) can also occur. The axial direction here means the direction in the optical axis of the image-producing system, i.e. the principal propagation direction of the light.

Three-dimensional localizations are known from so-called "particle tracking" experiments, such as those described in Kajo et al., 1994, Biophysical Journal, 67, Holtzer et al., 2007, Applied Physics Letters, 90, and Toprak et al., 2007, Nano Letters, 7(7). They have also been utilized already in image-producing methods that are based on the above-described switching and localization of individual molecules. Reference is made here to Huang et al., 2008, Science, 319, and Juette et al., 2008, Nature Methods. Reference regarding the existing art is further made to Bossi et al., 2008, Nano Letters, 8(8), 2463-2468 and to Pavani et al., 2009, PNAS, 106.

Localization of a point-like object in the Z direction can be accomplished in principle by evaluating that change in a light spot sensed on the detection surface of the camera which becomes visible when the point-like object moves out of the sharpness plane or focal plane optically conjugated with the detection surface. A point-like object is to be understood hereinafter as an object whose dimensions are smaller than the diffraction-limited resolution limit of the image-producing system, in particular of the detection objective. In this case the detection objective images an object of this kind into the image space in the form of a three-dimensional focus light distribution. The focus light distribution generates on the detection surface of the camera a light spot that is also referred to in the literature as a "point spread function," abbreviated PSF. If the point-like object is then moved through the focus in the Z direction, i.e. perpendicular to the plane of sharpness, the size and shape of the PSF then change. By analyzing the detected signal corresponding to the sensed light spot in terms of the size and shape of the PSF, inferences can be drawn as to the actual Z position of the object.

In the context of a three-dimensional localization, however, the basic problem exists that the PSF deriving from a point-like object is symmetrically in terms of the detection plane. This means that although the PSF changes when the point-like object is moved out of the sharpness plane, so that the spacing of the object from the plane of sharpness can be determined, the change in the PSF is nevertheless symmetrical on either side of the sharpness plane, so that it is impossible to decide which side of the sharpness plane the point-like object is located on.

Three-dimensional localization of point-like objects becomes even more difficult when so-called multicolor measurements needs to be carried out, in which the specimen is marked with different dyes and the detected signals sensed for these different dyes must be separated. Multicolor measurements are helpful in particular for co-localization of structures, for example proteins, inside a cell. If it is possible to separate the detected signals of the different dyes, a conclusion can then be drawn as to the respective distribution of the dyes and thus of the various structures.

A fundamental problem that occurs in high-resolution localization microscopy in the context of multicolor measurements is the so-called longitudinal chromatic aberration (also called axial chromatic aberration) exhibited to a certain degree by every detection objective. The longitudinal chromatic aberration is understood as an aberration which causes an object that emits light of different colors to be imaged in different image planes as a function of wavelength. This is illustrated in FIG. 1, in which it is assumed that a point-like object 10 is emitting light of two wavelengths (depicted in FIG. 1 respectively as a dashed and a dotted line and labeled 12 and 14). The longitudinal chromatic aberration that occurs in a detection optical system constituted by an objective 16 and a tube lens 18 now causes the focus light distributions generated by the detection optical system for the different wavelengths to be offset from one another in the Z direction. The center points of the mutually offset focus light distributions are labeled 20 and 22 in FIG. 1.

Longitudinal chromatic aberration is caused by the fact that the lens material exhibits dispersions, i.e. possesses different refractive indices for different wavelengths of light. Longitudinal chromatic aberration can be decreased to a certain extent by a skillful lens design. Typical high-performance objectives, for example, possess a longitudinal chromatic aberration of 150 to 200 nm, which means that a blue dye and a red dye that are located in the same plane of sharpness will be imaged with an offset of 150 to 200 nm from one another in the Z direction.

Longitudinal chromatic aberrations in the range recited above are tolerable in conventional microscopy, since the resolutions achievable in the Z direction are in any case only in a range from 600 to 1000 nm. On the other hand, however, very much better resolution values are now being achieved in localization microscopy, based on the detection of individual molecules. Resolutions below 50 nm, for example, are achievable. At such resolutions, a longitudinal chromatic aberration of the magnitude recited above is no longer tolerable.

SUMMARY

An embodiment of this invention provides a microscopic device for three-dimensional localization of point-like objects in a specimen, comprising: a detection optical system configured to image one or more point-like objects arranged in an object space, each in the form of a three-dimensional focus light distribution, into an image space; a detector unit arranged in the image space, configured to receive one light bundle from the detection optical system, the detector unit comprising a detection surface, arranged perpendicular to the incidence direction of the light bundle, configured to sense one or more light spots that each represent a planar section through the associated focus light distribution; and an evaluation unit configured, by evaluating the light spot sensed on the detection surface, to ascertain a lateral X-Y position of an associated point-like object within an object plane parallel to a sharpness plane, and an axial Z position of the associated point-like object relative to the sharpness plane in an optical axis direction located perpendicular to the sharpness plane, the sharpness plane being a plane, located in the object space, that is optically conjugated with a detection plane which is located in the image space and in which the detection surface is arranged, wherein, respectively, one Z-position correction value is stored for different wavelength regions detectable by the detector unit in the evaluation unit, which value indicates a longitudinal chromatic aberration of the detection optical system in that wavelength region, and wherein the evaluation unit is configured to correct the axial Z position, ascertained in a respective wavelength region, of a respective point-like object using an associated Z-position correction value, as well as a method of using the same.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following:

FIG. 3 shows an allocation protocol with which the shape of the PSF sensed on the detection surface is correlated with a Z position of a point-like object relative to a sharpness plane;

FIG. 4 schematically depicts a localization device according to an embodiment of the present invention;

FIG. 5 shows schematic depictions to illustrate a spectroscopic separation of different dyes; and FIG. 6 is a schematic depiction showing an alternative embodiment for evaluating the PSFs sensed on the detection surfaces.

DETAILED DESCRIPTION

Figure 1:
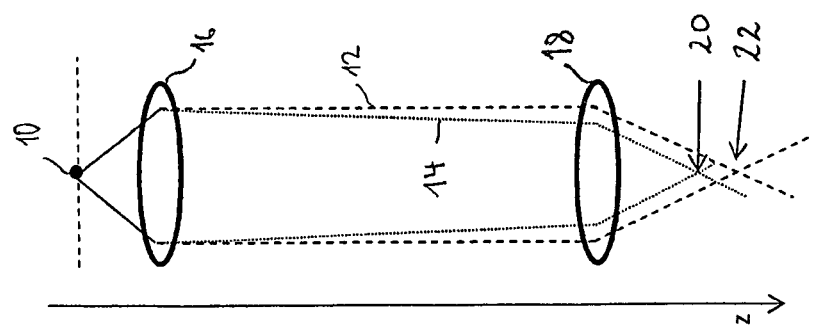
FIG. 1 is a schematic depiction to illustrate the longitudinal chromatic aberration occurring in a detection optical system.

An embodiment of this invention enables three-dimensional localization of point-like objects, based on a multicolor measurement, at high accuracy especially in the Z direction.

In a particularly advantageous embodiment, a device for three-dimensional localization of point-like objects in a specimen encompasses a detection optical system that images point-like objects arranged in an object space, each in the form of a three-dimensional focus light distribution, into an image space; a color separation apparatus that divides the light generated by the detection optical system for imaging the point-like objects into at least two separate light bundles whose light wavelengths lie in different wavelength regions; at least two detector units arranged in the image space, of which one detector unit receives one of the two light bundles and the other detector unit the other of the two light bundles, each detector unit comprising a detection surface, arranged perpendicular to the incidence direction of the respective light bundle, for sensing light spots that each represent a planar section through the associated focus light distribution; an evaluation unit that, by evaluating the respective light spot sensed on the respective detection surface, ascertains a lateral X-Y position of the associated point-like object within an object plane parallel to a sharpness plane, and an axial Z position of the associated point-like object relative to the sharpness plane in the direction of an optical axis located perpendicular to the sharpness plane, the respective sharpness plane being a plane, located in the object space, that is optically conjugated with a detection plane which is located in the image space and in which the respective detection surface is arranged; at least one Z-position correction value for at least one (preferably each) of the two wavelength regions being stored in the evaluation unit, which value indicates a longitudinal chromatic aberration of the detection optical system in that wavelength region; and the evaluation unit correcting the Z position, ascertained in the respective wavelength region, of the respective point-like object using the associated Z-position correction value.

The device according to an embodiment of the present invention is suitable for carrying out multicolor measurements for three-dimensional localization of point-like objects with high spatial resolution, in particular including in the Z direction. For this, the localization device comprises a color separation apparatus that divides the light emitted from the specimen into at least two wavelength regions. If dyes whose emission spectra overlap only slightly are used in the context of the multicolor measurement, the color separation apparatus can be implemented by suitable selection of color filters in the detection beam path of the device. In this case a separate detection filter, and thus a separate detection channel, is allocated to each dye. The number of dyes that can be separated in this manner is limited by the fact that the emission spectra of the dyes should if possible fit without major overlap into the available spectral window of visible light.

Effective color separation is, however, possible even with only exactly two detection channels. In this case the color separation apparatus encompasses, for example, a dichroic beam splitter that splits the light generated by the detection optical system for imaging the point-like objects, regardless of the number of dyes to be separated, into only exactly two separate light bundles that are each incident onto a detector unit. In this fashion, images of one and the same object in different wavelength regions are sensed on the detection surfaces of the two detector units. The dye can then easily be determined based on the ratio of the brightnesses of these two light spots. Be it noted at this juncture that the two detector units can also be combined into one unit, e.g. in the form of a camera in which one portion of the camera chip is used for the one detection channel and another portion of the camera chip for another detection channel.

According to an embodiment of the present invention, the lateral X-Y position as well as the axial Z position of the particular point-like object in question are ascertained by evaluating the light spot sensed on the detection surface of the respective detector unit. This evaluation contains, for example, an analysis of the shape and size of the PSF yielded by the light spot, in order to determine the Z position of the point-like object relative to the sharpness plane. For this it is conceivable, for example, to base the analysis on a suitable allocation protocol that allocates the correct Z position to a specific measured shape of the PSF. An allocation protocol of this kind can be obtained, for example, by means of calibration measurements in which a point-like object is moved in the Z direction from one side to the other side of the sharpness plane, and the shape of the PSF is determined for the now known Z positions. This yields an allocation protocol that makes it possible, in subsequent measurements, to allocate the correct Z position to the measured PSF shape.

For example, an allocation protocol can be used in which the difference in the dimensions of the PSF in the X direction and Y direction is correlated with the Z position.

According to an embodiment of the present invention the evaluation unit retains, for each of the at least two wavelength regions, at least one Z-position correction value that indicates a longitudinal chromatic aberration of the detection optical system in the respective wavelength region. This makes it possible to correct the Z position of the object, ascertained in the manner described above, with a wavelength-dependent Z-position correction value so as thereby to compensate for the longitudinal chromatic aberration occurring in the detection optical system. The invention can thus make possible highly accurate localization of different dyes in the Z direction as well.

In a particularly preferred embodiment, an apparatus is provided which influences the respective focus light distribution in such a way that the associated light spot has a symmetrical shape when the point-like object is located in the sharpness plane; that the associated light spot has a first asymmetrical shape when the point-like object is located on the side of the sharpness plane facing away from the detection optical system; and that the associated light spot has a second asymmetrical shape, distinguishable from the first symmetrical shape, when the point-like object is located on the side of the sharpness plane facing toward the detection optical system. With this configuration a symmetry breakage is implemented in such a way that a light spot, sensed on the detector surface, which derives from a point-like object that is located on the one side of the sharpness plane differs from a light spot that originates from an object on the other side of the sharpness plane. "Symmetrical" hereinafter means a state in which the light spot is symmetrical with respect to reflections at the X-Z plane and the Y-Z plane, which planes are both arranged perpendicular to the detection surface arranged in the X-Y plane.

The apparatus for influencing the respective focus light distribution preferably encompasses a cylindrical lens. A cylindrical lens of this kind generates an astigmatic aberration that causes an asymmetrical change in the PSF when the point-like object is moved from one side of the sharpness plane to the other side. If the object is located in the sharpness plane, however, the PSF is then symmetrical (e.g. slightly cruciform). The exact Z position of the object can easily be determined on the basis of the asymmetrical change, caused by the astigmatic aberration, in the PSF shape on the detection surface, i.e. in the lateral direction.

When a cylindrical lens is used, the sharpness planes allocated to the two detection surfaces can coincide in the object space. It is likewise possible, however, for the symmetry breakage of the PSF provided in order to determine the Z position to be achieved by the fact that the sharpness planes allocated to the two detection surfaces are offset from one another in the object space. In this embodiment, if an object to be localized is located in the sharpness plane of the one detection channel it is imaged sharply there, while it is imaged unsharply in the other detection channel. If the object is arranged between the two sharpness planes, it is imaged unsharply onto both detection channels, but more sharply on that channel whose focus position is closer than on the other channel. Because it is known which detection channel occupies which focus position, here as well it is possible to decide, on the basis of a measurement, the Z position in which the point-like object is located. A suitable allocation protocol can once again be obtained from calibration measurements. One conceivable allocation protocol here would be, for example, the difference between the diameter of the light spot sensed in the one detection channel and the diameter of the light spot sensed in the other detection channel.

The symmetry breakage according to an embodiment of the present invention of the PSF can also be implemented differently, for example in accordance with the so-called double helix method that is described in Pavani et al., 2009, PNAS, 106.

A positioning apparatus for moving a specimen carrier and/or the detection optical system, in particular the detection objective, along the optical axis is preferably provided. This makes it possible to displace the specimen, and thus the point-like objects to be localized, in the Z direction, i.e. in the direction of the optical axis, relative to the sharpness plane of the detection optical system in order to determine the (asymmetrical) change in the shape of the PSF allocated to the respective object, and to ascertain therefrom the Z position of the object.

The localization device according to an embodiment of the present invention preferably has a light source for emitting excitation light onto the specimen, and an apparatus, located after the light source, for spectral variation of the excitation light. The fact that the excitation light emitted onto the specimen can be varied in terms of its spectral composition makes it possible, for example by the use of reflective calibration members, to accurately determine the longitudinal chromatic aberrations of the detection optical system for those wavelengths, and to retain, in the form of the Z-position correction, values that can be introduced into later measurements of the dyes to be localized.

In an advantageous refinement of the method according to an embodiment of the present invention, provision is made for illuminating a calibration specimen, which contains at least one reflective or scattering point-like calibration object, with light of different calibration wavelengths; ascertaining for each calibration wavelength the Z position of the point-like calibration object; determining the deviations between the Z positions of the calibration object ascertained for the various calibration wavelengths; and identifying the wavelength-dependent Z-position correction values on the basis of those deviations. This advantageous embodiment involves performing a calibration in order to identify the Z-position correction values indicating the longitudinal chromatic aberrations by using a calibration specimen, e.g. a glass substrate, on or in which are located reflective or scattering calibration objects such as, for example, gold microspheres or metallic nanodots. In order to determine the longitudinal chromatic aberrations, the calibration objects can be irradiated with the same light distribution exhibited, in terms of their emission, by the dyes that will subsequently be localized. The calibration objects thus light up at the same wavelength as the dyes that will later be investigated. The calibration objects can then be illuminated successively with the desired wavelengths. The Z position of the calibration object in question is then determined for each wavelength. It is possible in this context to carry out, for each individual calibration wavelength, multiple calibration measurements for different Z positions of the calibration specimen. Similarly, a specific Z position of the calibration specimen can be traveled to in order then to set the various calibration wavelengths at that Z position. In any case, the necessary calibration information can thereby be generated, for example, in the form of calibration curves for the different dyes.

The method described above has the advantage that different dye combinations do not need to be kept on hand as reference specimens, but instead only one calibration specimen is required. All that is necessary is to generate a corresponding excitation light distribution for each dye that is to be localized. This can be accomplished, for example, using suitable filters arranged after the light source that emits the excitation light. In this case each dye type has allocated to it a filter which generates a light spectrum that corresponds to the emission spectrum of the dye.

Z-position correction values for wavelengths that lie between each two calibration wavelengths are preferably ascertained by interpolation of the identified Z-position correction values. Additionally or alternatively, Z-position correction values for wavelengths that are longer than the longest calibration wavelength or shorter than the shortest calibration wavelength can be ascertained by extrapolation of the identified Z-position correction values. These advantageous refinements make it possible to determine longitudinal chromatic aberrations even for a wavelength region for which a calibration measurement has not been carried out.

Figure 2:
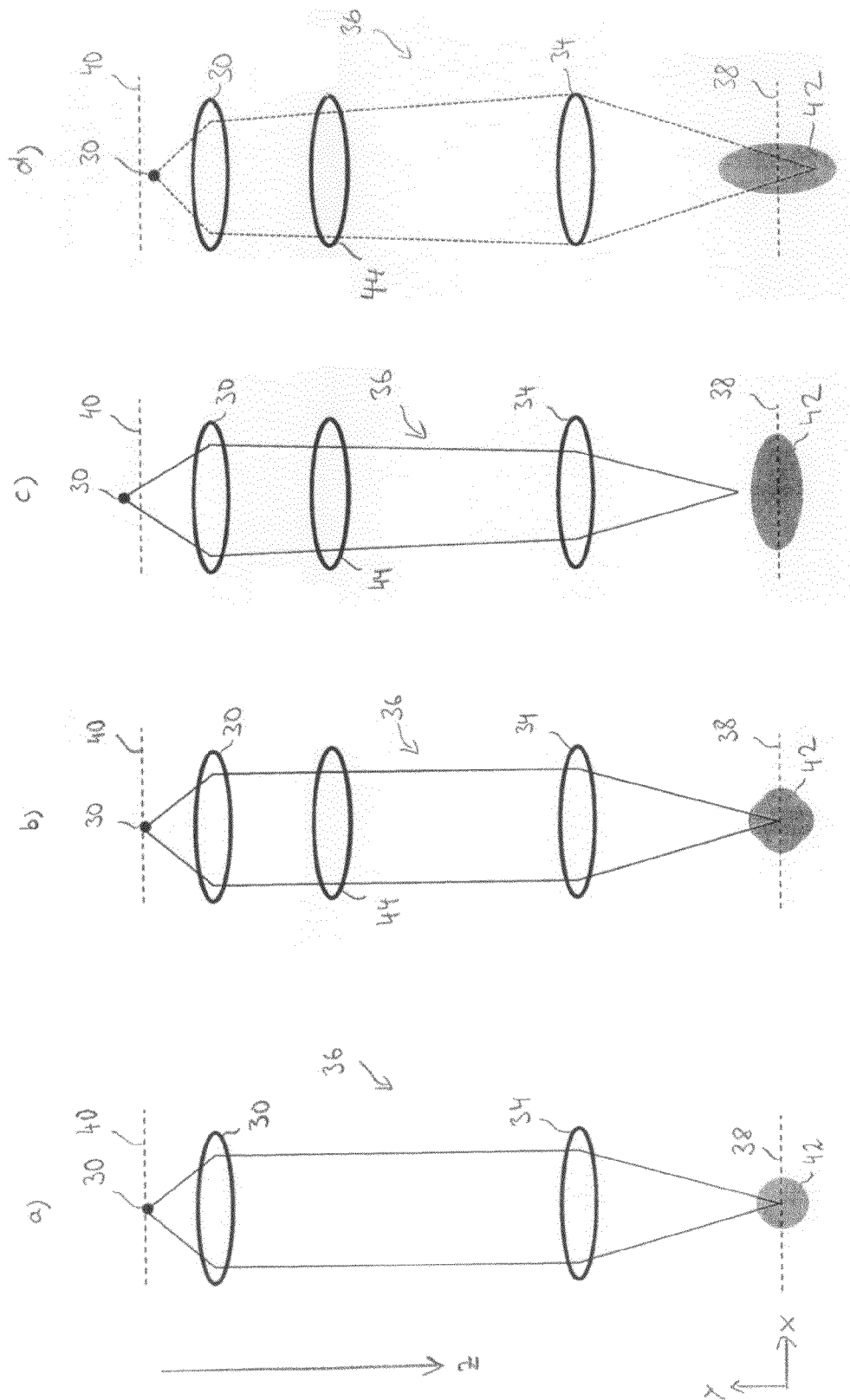
FIG. 2 shows schematic depictions to illustrate how a cylindrical lens causes a symmetry breakage of a PSF sensed on a detection surface.

Referring to FIG. 2, an explanation will firstly be given of how the Z position of a point-like object is ascertained in an embodiment of the present invention by evaluation of a PSF sensed on a detection surface. Only monochromatic light will be considered initially for the instances shown in FIG. 2, in order to simplify the explanation.

FIG. 2 shows in part a) a conventional arrangement in which a point-like object 30 is imaged onto a detection surface 38 via a detection optical system 36 constituted from an objective lens 32 and a tube lens 34. Object 30 is assumed here to be located in a sharpness plane 40 that is a plane optically conjugated with detection plane 38.

Detection optical system 36 shapes the light proceeding from object 30 into a three-dimensional focus light distribution that is incident onto detection surface 38. Detection surface 38 thus senses a light spot 42 that represents a planar section, located perpendicular to the Z direction, through the focus light distribution. In order to illustrate the situation better, light spot 42 is depicted in FIG. 2 in a plan view onto detection surface 38, i.e. in the X-Y plane. In the instance depicted in part a) of FIG. 2, in which the point-like object 30 is located in sharpness plane 40, light spot 42 on detection surface 38 has a circular shape, i.e. a shape that is symmetrical with respect to reflections at the X-Z plane and the Y-Z plane.

FIG. 2 shows in part b) a modified embodiment in which a cylindrical lens 44 is provided in addition to objective lens 32 and tube lens 34. Cylindrical lens 44 has different refractive powers in the X-Y direction. Light spot 42 on detection surface 38 is correspondingly deformed into a cross shape in the X and Y directions. Because the point-like object 30 is still located in sharpness plane 40 in the instance depicted in part b), however, the cruciform light spot 42 remains symmetrical in the sense indicated above.

FIG. 2 shows in part c) an instance in which the point-like object 30 is arranged above sharpness plane 40. This offset out of sharpness plane 40 causes light spot 42 on detection plane 38 to be deformed asymmetrically into an ellipse. The greater the distance of object 30 from the sharpness plane, the more pronounced the elliptical shape of light spot 42 becomes.

FIG. 2 shows in part d) an instance in which the point-like object 30 is located below sharpness plane 40. Here as well, light spot 42 on detection surface 38 is elliptically deformed, but in an orientation that is different from the orientation of light spot 42 in part c). It is correspondingly possible to detect, based on the shape of light spot 42, whether the point-like object is arranged above or below sharpness plane 40.

As is apparent from what is depicted in FIG. 2, the Z position of the point-like object 30 relative to sharpness plane 40 can be determined on the basis of the shape and dimensions of light spot 42 on detection surface 38. This is accomplished in the present exemplifying embodiment on the basis of an allocation protocol that is depicted by way of example in FIG. 3. This allocation protocol is obtained by means of calibration measurements in which the point-like object 30 is displaced in the Z direction and the shape of light spot 42, i.e. the shape of the PSF, is determined respectively for individual Z positions. In the case of the allocation protocol depicted in FIG. 3, the difference in the lengths of the two mutually perpendicular ellipse axes $PSF_x$ and $PSF_y$ is utilized as a parameter for the shape of the PSF, and is compared with the Z positions. As is immediately apparent from what is depicted in FIG. 3, one Z position can be unequivocally allocated to each value of the difference $PSF_x - PSF_y$. If the value of the aforesaid difference is zero, it may be inferred therefrom that the point-like object 30 is located exactly in sharpness plane 40.

Strictly speaking, the allocation protocol depicted in FIG. 3 is valid only for a single predetermined wavelength. If what is considered is not just a single wavelength but several different wavelengths or wavelength regions, the result is then several allocation protocols that are displaced and possibly also deformed as a result of longitudinal chromatic aberration as compared with the allocation protocol depicted in FIG. 3. The longitudinal chromatic aberration essentially produces a displacement of the zero crossing shown in FIG. 3. According to an embodiment of the present invention, an allocation protocol of the kind shown in FIG. 3 is therefore ascertained, in the context of a calibration measurement, for every wavelength of interest. From the aforesaid displacements of the zero crossings of the calibration curves obtained in this fashion, Z-position correction values which represent the longitudinal chromatic aberration of the detection optical system for the respective wavelengths are then derived, and are taken into account when determining the Z positions of the point-like objects.

FIG. 4 shows a microscopic device 100 that represents an exemplifying embodiment of the present invention.

Device 100 has an excitation light source 102 that emits excitation light onto an apparatus 104 that serves for spectral variation of the excitation light. Apparatus 104 encompasses, for example, an arrangement of several optical filters that can be introduced selectably into the beam path of the excitation light.

The excitation light emitted from apparatus 104 is incident onto a dichroic beam splitter 106 which is embodied so that it reflects the excitation light toward an objective 108. Objective 108 delivers the excitation light onto a specimen 112, arranged on a movable specimen holder 110, that contains a plurality of point-like objects that are to be localized. Of these objects, only a single object, labeled 114, is depicted purely schematically in FIG. 4. The dimensions of the point-like object 114 are assumed here to be smaller than the diffraction-limited resolution limit of objective 108. Specimen holder 110 is coupled to a positioning apparatus 116 which serves to displace specimen holder 110 along an optical axis O.

The light proceeding from the point-like object 114 is guided through objective 108 and is incident onto beam splitter 106. Beam splitter 106 is embodied so that it transmits the light proceeding from object 114 onto a detection filter 118. The light then passes through a tube lens 120 and is incident onto a deflection mirror 122. The light reflected at deflection mirror 122 then passes through a cylindrical lens 124 by which the light is influenced in the manner illustrated in FIG. 2.

After passing through cylindrical lens 124, the light passes into a color separation apparatus 126. Color separation apparatus 126 contains a dichroic beam splitter 128 whose effect will be explained in further detail later on with reference to FIG. 5, part a). Dichroic beam splitter 128 allows a portion of the fluorescent light within a first wavelength region to pass, while it reflects the remaining portion of the fluorescent light within a second wavelength region (see also part a) of FIG. 5). The portion of the fluorescent light that is allowed to pass is directed via an arrangement of deflection mirrors 130, 132, 134, and 136 onto a camera 138. The portion of the fluorescent light reflected at beam splitter 128 is directed on a different light path, via an arrangement of deflection mirrors 140, 142, and 144, once again onto camera 138. Camera 138 comprises two separate detector units 146 and 148 each having a detection surface 150 and 152, respectively. The portion of the fluorescent light allowed to pass by beam splitter 128 is incident onto detection surface 150, while the portion of the fluorescent light reflected at beam splitter 128 is incident onto detection surface 152. The color separation apparatus thus splits the detection beam path, by means of dichroic beam splitter 128, into two separate detection channels, one of which leads to detection surface 150 and the other to detection surface 152.

Device 100 further comprises a controller 154 that applies control to the individual components of device 100 and performs the evaluation according to an embodiment of the present invention of the signals generated by camera 138 in order to localize the point-like object 114.

Color separation apparatus 126 makes possible a spectroscopic separation of different dyes contained in specimen 112, which separation will be explained below with reference to FIG. 5.

FIG. 5 shows in part a) the fluorescence emission of three different dyes A, B, and C, as well as the transmission characteristic curve, labeled 160, of dichroic beam splitter 128. As explained earlier, dichroic beam splitter 128 splits the detection beam path into two separate detection channels that lead to the two separate detection surfaces 150 and 152. Because the sharpness planes allocated to the two detection surfaces 150 and 152 are coincident in the object space, detection surfaces 150 and 152 sense the exact same region within specimen 112. The wavelength regions that travel into the two detection channels are, however, different. For example, the emission region of dye A is located almost entirely in the one detection channel, while the emission region of dye C is located almost entirely in the other detection channel. The emission region of dye B is located approximately in the middle of the two detection channels.

When the fluorescent light proceeding from an individual dye is then received, the fluorescent light is thus distributed over the two detection channels in the manner shown in part a) of FIG. 5. FIG. 5 shows, in part b), examples of light spots that originate from the three dyes A, B, and C and are sensed on detection surfaces 150 and 152. As may be gathered from this depiction, dye A leaves behind in the one detection channel a light spot having a comparatively high signal level, while it produces in the other detection channel a light spot having a relatively low signal level. The light spot caused by dye C exhibits the opposite behavior. The light spot originating from dye B, on the other hand, has approximately the same signal level in both detection channels.

For each individual-molecule signal, the brightness distribution, i.e. the distribution of the photons over the two detection channels, can be measured and can be presented in a diagram shown in part c) of FIG. 5. Each measured individual-molecule event generates in this diagram a measurement point that is defined by the polar coordinates r and φ. The angle φ provides information here as to the color of the dye, and the distance r from the origin of the coordinate system indicates brightness. When a very large number of events are measured from all three dyes A, B, and C, the result is the distribution shown in part c), which is notable for three "dye clouds" that can be separated from one another. The spatial extent of these dye clouds is defined by the statistical variation of the distribution of the photons in the respective detection channels, and by the fact that the individual-molecule events all have different brightnesses, so that the total number of photons per event is also random. When an event that falls, in terms of its photon distribution, into the region of one of these dye clouds is then measured, it is possible to establish unequivocally that the molecule is one of dye type A, B, or C.

The result is that the number of dyes that can be separated from one another is considerably greater than the number of detection channels required. In addition, it is possible to separate from one another dyes whose emission spectra substantially overlap each other. This is highly advantageous, since all dyes are illuminated with the same excitation light. It should also be mentioned that the combination of spectroscopic signal separation explained above with reference to FIG. 5, and three-dimensional localization, yields additional usable information that can be used to determine the longitudinal chromatic aberration. For example, the fact that the signal is separated into two spectrally different detection channels causes the longitudinal chromatic aberration to have a different effect in each detection channel. The signal for one and the same individual-molecule event will thus look different in the one detection channel than in the other detection channel. If the same allocation protocol, based on which the Z position is inferred from the shape of the PSF, is utilized for both signals, different values for the Z position will then be obtained for the two detection channels. The distribution of the dye spectra, and thus the absolute longitudinal chromatic aberration, can be inferred from these two values.

The spectroscopic signal separation explained with reference to FIG. 5 has a further advantage. Specifically, if the dye clouds depicted in part c) of FIG. 5 are measured, it is evident that the width of the respective dye clouds is usually greater than would be expected from purely statistical considerations. The reason for this is that changes in the micro-environment of a dye can result in changes in the emission spectrum. Depending on the nature of the immediate environment of a dye, a dye molecule at one location in the specimen can therefore have a different spectrum than at another location. Spectroscopic signal separation offers the advantage that this spectroscopic shift can be individually measured for each individual dye molecule, and the longitudinal chromatic aberration can thus also be correspondingly corrected for each individual molecule.

The embodiment described above is to be understood as merely an example. One of these possible variants is depicted in FIG. 6.

FIG. 6 shows an arrangement having two separate detection channels, one of which is defined substantially by an objective 170 and a tube lens 172, and the other by objective 170 and a tube lens 174. Light proceeding from a point-like object 180 is directed by a beam splitter 182 and by deflection mirrors 184, 186, and 187 in equal portions into the two detection channels. The two detection channels differ slightly in terms of their focus position. This means that the one detection channel has a first image plane 188 that is optically conjugated with a first sharpness plane 190, while the other detection channel has a second image plane 192 that is offset in the Z direction with respect to first image plane 188 and is optically conjugated with a second sharpness plane 194 that in turn is offset in the Z direction with respect to first sharpness plane 190. If object 180 to be localized is located in the sharpness plane of the one detection channel, it is imaged sharply therein, while it is imaged unsharply in the other detection channel. If it is located between the two sharpness planes 190 and 194, it is imaged unsharply in both detection channels. If object 180 is arranged beyond both focal planes 190 and 194, it is imaged unsharply in both detection channels, but more sharply in that detection channel whose sharpness plane is closer to object 180 than in the other.

Since it is known a priori which detection channel is in which focus position, here as well it is possible to decide on the basis of a measurement where object 180 is located. A suitable allocation protocol can once again be obtained from calibration measurements. One conceivable allocation protocol here would be, for example, the difference between the diameter of light spot 198 sensed in the one detection channel and the diameter of light spot 200 sensed in the other detection channel. An allocation protocol of this kind is similar to the allocation protocol depicted in FIG. 3.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the attached claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B." Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise.

The invention claimed is:

1. A microscopic device for three-dimensional localization of point-like objects in a specimen, comprising:
a detection optical system configured to image one or more point-like objects arranged in an object space, each in the form of a three-dimensional focus light distribution, into an image space;
a detector unit arranged in the image space, configured to receive one light bundle from the detection optical system, the detector unit comprising a detection surface, arranged perpendicular to the incidence direction of the light bundle, configured to sense one or more light spots that each represent a planar section through the associated focus light distribution; and
an evaluation unit configured, by evaluating the light spot sensed on the detection surface, to ascertain a lateral X-Y position of an associated point-like object within an object plane parallel to a sharpness plane, and an axial Z position of the associated point-like object relative to the sharpness plane in an optical axis direction located perpendicular to the sharpness plane, the sharpness plane being a plane, located in the object space, that is optically conjugated with a detection plane which is located in the image space and in which the detection surface is arranged, wherein, respectively, one Z-position correction value is stored for different wavelength regions detectable by the detector unit in the evaluation unit, which value indicates a longitudinal chromatic aberration of the detection optical system in that wavelength region, and wherein the evaluation unit is configured to correct the axial Z position, ascertained in a respective wavelength region, of a respective point-like object using an associated Z-position correction value.

2. The microscopic device of claim 1, further comprising: a filter configured to filter out excitation light, emitted by a light source, from the light bundle received by the detector unit.

3. The microscopic device of claim 1, further comprising: a color separation apparatus configured to divide light generated by the detection optical system into at least a first and a second separate light bundle whose light wavelengths lie in different wavelength regions, wherein the detector unit comprises at least a first and a second image space detector unit arranged in the image space, of which the first image space detector unit is configured to receive the first light bundle and the second image space detector unit is configured to receive the second light bundle, each image space detector unit comprising a detection surface, arranged perpendicular to an incidence direction of a respective light bundle, configured to sense the light spots that each represent a planar section through an associated focus light distribution.

4. The microscopic device of claim 1, further comprising: a distribution apparatus configured to influence respective focus light distribution in such a way that (i) an associated light spot has a symmetrical shape when the point-like object is located in the sharpness plane, (ii) the associated light spot has a first asymmetrical shape when the point-like object is located on a side of the sharpness plane facing away from the detection optical system, and (iii) the associated light spot has a second asymmetrical shape, distinguishable from the first symmetrical shape, when the point-like object is located on a side of the sharpness plane facing toward the detection optical system.

5. The microscopic device of claim 4, wherein a respective asymmetrical shape approximates the shape of an ellipse, and wherein the evaluation unit is configured to ascertain the axial Z position of a respective point-like object based on the difference in lengths of two mutually perpendicular ellipse axes.

6. The microscopic device of claim 4, wherein the distribution apparatus comprises a cylindrical lens.

7. The microscopic device of claim 3, wherein sharpness planes allocated to two detection surfaces are coincident in the object space.

8. The microscopic device of claim 3, wherein sharpness planes allocated to two detection surfaces are offset from one another in the object space.

9. The microscopic device of claim 8, wherein the two detection surfaces are configured to sense light spots that belong to one and the same point-like object, and wherein the evaluation unit is configured to ascertain the axial Z position of that point-like object based on a size ratio of the light spots.

10. The microscopic device of claim 3, wherein the color separation apparatus comprises a dichroic beam splitter.

11. The microscopic device of claim 3, wherein the evaluation unit is configured to ascertain a color of a respectively imaged point-like object based on a ratio of brightnesses of light spots sensed by two detection surfaces and belonging to that respectively imaged point-like object, to obtain an ascertained color, and wherein the evaluation unit is configured to assign the ascertained color to an associated Z-position correction value that indicates a longitudinal chromatic aberration for that ascertained color.

12. The microscopic device of claim 1, further comprising: a positioning apparatus configured to move a specimen carrier, the detection optical system, or the specimen carrier and the detection optical system, along the optical axis.

13. The microscopic device of claim 1, further comprising: a light source configured to emit excitation light onto the specimen; and an spectral variation apparatus, arranged after the light source, configured to spectrally vary the excitation light delivered onto the specimen.

14. A method for three-dimensionally localizing point-like objects in a sample, the method comprising:

imaging one or more point-like objects arranged in an object space, each in the form of a three-dimensional focus light distribution, into an image space by a detection optical system;

receiving a light bundle from the detection optical system by at least one detector unit arranged in the image space, the detector unit comprising a detection surface, arranged perpendicular to an incidence direction of the light bundle, configured to sense one or more light spots that each represent a planar section through an associated focus light distribution;

ascertaining a lateral X-Y position of a respective point-like object within an object plane parallel to a sharpness plane, and an axial Z position of the respective point-like object relative to the sharpness plane in an optical axis direction located perpendicular to the sharpness plane, by evaluating an associated light spot sensed on the detection surface, the sharpness plane being a plane, located in the object space, that is optically conjugated with a detection plane which is located in the image space and in which the detection surface is arranged;

making available one respective Z-position correction value for different wavelength regions detectable by the detector unit, the respective Z-position correction value indicating a longitudinal chromatic aberration of the detection optical system in an associated wavelength region; and correcting the axial Z position, ascertained in the associated wavelength region, of the respective point-like object using the respective Z-position correction value.

15. The method of claim 14, further comprising:
filtering out excitation light emitted by a light source by a filter from the light bundle received by the detector unit.

16. The method of claim 14, further comprising:
dividing generated light, which is generated by the detection optical system, into at least a first and a second light bundle, which are separate, and whose light wavelengths lie in different wavelength regions;

receiving the first light bundle by a first image space detector unit, and receiving the second light bundles by a second image space detector unit, each detector unit being arranged in the image space and comprising a detection surface, arranged perpendicular to an incidence direction of a respective light bundle, for sensing light spots that each represent a planar section through an associated focus light distribution.

17. The method of claim 14, further comprising:
(a) illuminating a calibration specimen comprising a reflective or scattering point-like calibration object with light of different calibration wavelengths;
(b) ascertaining the axial Z position of the point-like calibration object for each calibration wavelength;
(c) determining deviations between axial Z positions of the calibration object ascertained for the various calibration wavelengths; and
(d) identifying wavelength-dependent Z-position correction values based on the deviations.

18. The method of claim 14, further comprising:
(a) illuminating a point-like calibration object comprising a plurality of different fluorescent dyes with light of different excitation wavelengths, wherein each excitation wavelength excites respectively one fluorescent dye allocated thereto for emitting fluorescent light, the fluorescent wavelength of which differs from the fluorescent wavelengths of the fluorescent light emitted by the other fluorescent dyes;
(b) ascertaining the axial Z position of the point-like calibration object for each fluorescent wavelength which defines a calibration wavelength;
(c) determining deviations between axial Z positions of the point-like calibration object ascertained for the various calibration wavelengths; and
(d) identifying wavelength-dependent Z-position correction values based on the deviations.

19. The method of claim 18, further comprising:
(i) ascertaining Z-position correction values for wavelengths that lie between each two calibration wavelengths by interpolating identified Z-position correction values
(ii) ascertaining Z-position correction values for outside Z-position correction values, for wavelengths that are longer than the longest calibration wavelength or shorter than the shortest calibration wavelength, by extrapolating the identified Z-position correction values, or
both (i) and (ii).

* * * * *